(12) United States Patent
Bajic et al.

(10) Patent No.: US 9,982,307 B2
(45) Date of Patent: May 29, 2018

(54) METHYLATION BIOMARKERS FOR BREAST CANCER

(71) Applicant: KING ABDULLAH UNIVERSITY OF SCIENCE AND TECHNOLOGY, Thuwal (SA)

(72) Inventors: Vladimir Bajic, Thuwal (SA); Hicham Mansour, Thuwal (SA); Roberto Incitti, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 393 days.

(21) Appl. No.: 14/408,230

(22) PCT Filed: Jun. 11, 2013

(86) PCT No.: PCT/IB2013/002012
§ 371 (c)(1),
(2) Date: Dec. 15, 2014

(87) PCT Pub. No.: WO2013/186639
PCT Pub. Date: Dec. 19, 2013

(65) Prior Publication Data
US 2015/0141262 A1      May 21, 2015

Related U.S. Application Data

(60) Provisional application No. 61/659,239, filed on Jun. 13, 2012.

(51) Int. Cl.
*C12Q 1/68*          (2018.01)
(52) U.S. Cl.
CPC ..... *C12Q 1/6886* (2013.01); *C12Q 2600/154* (2013.01); *C12Q 2600/172* (2013.01)
(58) Field of Classification Search
None
See application file for complete search history.

(56) References Cited

U.S. PATENT DOCUMENTS

| | | |
|---|---|---|
| 2009/0280478 A1 | 11/2009 | Polyak et al. |
| 2010/0130527 A1 | 5/2010 | Lehrer et al. |
| 2011/0150979 A1 | 6/2011 | Ray et al. |

FOREIGN PATENT DOCUMENTS

| | | |
|---|---|---|
| WO | WO 2006/008128 A2 | 1/2006 |
| WO | WO2009/108917 A2 | 9/2009 |
| WO | 2013/124740 | 8/2013 |
| WO | 2013/186639 | 12/2013 |

OTHER PUBLICATIONS

Kamalakaran (Molecular One (2011) 77-92; available on line Dec. 2, 2010.*
Hill et al. (Cancer Res; 71(8) Apr. 15, 2011).*
Costello et al. Journal of Biological Chemistry. vol. 269, No. 25, Issue of Jun. 24, pp. 1722g-17237, 1994.*
Hesselink et al. Clin Cancer Res 2011; 17:2459-2465.*
van Eijk et al. BMC Genomics 2012, 13:636, thirteen pages.*
Wu J Pathol 2001; 195: 53-65.*
Newton et al (2001) Journal of Computational Biology, vol. 8, No. 1, 2001, pp. 37-52.*
Slonin, Nature Genetics Supplement, vol. 32, Dec. 2002, pp. 502-508.*
Baker. Journal of the National Cancer Institute, vol. 95, No. 7, Apr. 2, 2003.*
Whitehead (Genome Biology 2005 vol. 6 Issue 2 Article R13).*
Bock (Epigenomics 2009 vol. 1 No. 1 pp. 99-110).*
Michels (Experimental Gerontology 2010 vol. 45 pp. 297-301).*
Kamalakaran, et al., "DNA methylation patterns in luminal breast cancers differ from non-luminal 1-2\ subtypes and can identify relapse risk independent of other clinical variables," *Molecular Oncology* (Dec. 2, 2010) vol. 5 pp. 77-92.
Kim, et al., "Downregulation of ARFGEF1 and CAMK2B by promoter hypetmethylation in breast 1-2 \,cancer cells," *BMB Reports* (2011) 44(8) pp. 523-528.
Muggerud, et al., "Frequent aberrant DNA methylation of ABCB1, FOXC1, PPP2R2B and PTEN 1-2'. in ductal carcinoma in situ and early invasive breast cancer," *Breast Cancer Research* (2010) pp. 1-10.
International Search Report for PCT/IB2013/002012 dated Apr. 8, 2014.
International Preliminary Report on Patentability for PCT/IB2013/002012 dated Dec. 24, 2014.
"Breast Cancer Incidence, Mortality and Prevalence Worldwide in 2008", Summary Globocan (2008). obtained from http://globocan.iarc.fr/old/FactSheets/cancers/breast-new.asp on Aug. 3, 2017. three pages.
Cottrell, S., "Molecular Diagnostic Applications of DNA Methylation Technology", Clinical Biochemistry 37 (2004) pp. 595-604.
Esserman, L., et al., "Rethinking Screening for Breast Cancer and Prostate Cancer", JAMA, 302:1685-1692 (2009).
Graham, et al., British Journal of Cancer, 102, 1284-1293 (2010).
Kalager, M., et al., "Effect of Screening Mammography on Breast-Cancer Mortality in Norway", NEJM, 363:1203-10 (2010).
Mandelblatt, J.S., et al., "Effects of Mammography Screening Under Different Screening Schedules: Model Estimates of Potential Benefits and Harms", Ann Intern Med, 151:738-47 (2009).
Melnikov, Anatoliy A. et al., "Array-Based Multiplex Analysis of DNA Methylation in Breast Cancer Tissues", Journal of Molecular Diagnostics, The American Society for Investigative Pathology, vol. 10, No. 1, pp. 93-101, Jan. 12 (2008).
Newman, David, H., NEJM, 366 (2):191, Author Reply 191-2, Jan. 12 (2012).

(Continued)

*Primary Examiner* — Juliet C Switzer
(74) *Attorney, Agent, or Firm* — Smith, Gambrell & Russell, LLP

(57) ABSTRACT

Different combinations of methylation status based biomarkers can be used to test for breast cancer with high sensitivity and high specificity.

2 Claims, No Drawings

(56) References Cited

OTHER PUBLICATIONS

Olek, A, et al., "A Modified and Improved Method for Bisulphate Based Cytosine Methylation Analysis", Nucleic Acids Res., 24 (24): 5064-6, Dec. 15 (1996).
Rein, T., et al., "Identifying 5-Methylcytosine and Related Modifications in DNA Genomes", Nucleic Acid Res., 26(10): 2255-64, May 15 (1998).
Ronneberg, Jo Anders, et al., "Methylation Profiling with a Panel of Cancer Related Genes: Association with Estrogen Receptor, TP53 Mutation Status and Expression Subtypes in Sporadic Breast Cancer", Molecular Oncology, Elsevier, Amsterdam, NL, vol. 5, No. 1, pp. 61-76, Nov. 18 (2010).
Siegel, R., et al., "Cancer Statistics", CA Cancer J Clin, 62 (1):Jan. 10-29 (2012).
Triphati, Anusri, et al., Int J Cancer, 122, 1557-1566 (2008).
Valentin, Mev Dominguez, et al., "Molecular Insights on Basal-Like Breast Cancer", Breast Cancer Research and Treatment, Kluwer Academic Publishers, BO, vol. 134, No. 1, pp. 21-30, Jan. 11 (2012).
Van Der Auwera, Ilse, et al., "Array-Based DNA Methylation Profiling for Breast Cancer Subtype Discrimination", PLoS ONE, vol. 5, No. 9, p. e126161, January (2010).
Welch, H.G., M.D., M.P.H., NEJM, 363:1276-1278, Sep. 23 (2010).

\* cited by examiner

US 9,982,307 B2

METHYLATION BIOMARKERS FOR BREAST CANCER

CLAIM OF PRIORITY

This application claims the benefit under 35 U.S.C. 371 to International Application No. PCT/IB2013/02012, filed Jun. 11, 2013, which claims priority to U.S. Provisional Patent Application No. 61/659,239, filed Jun. 13, 2012, each of which is incorporated by reference in its entirety.

TECHNICAL FIELD

This invention relates to methylation biomarkers for breast cancer.

BACKGROUND

Breast cancer is the most frequent cancer among women both in developed and developing countries, with an estimated 1.38 million new cancer cases diagnosed in 2008 worldwide (23% of all cancers). Incidence rates vary from 19.3 per 100,000 women in Eastern Africa to 89.7 per 100,000 women in Western Europe. Rates are high (greater than 80 per 100,000) in all developed regions of the world except in Japan. However, rates are low (less than 40 per 100,000) in most of the developing regions. The range of mortality rates is much smaller (approximately 6-19 per 100,000) because of the more favorable survival rate in developed regions. As a result, breast cancer ranks as the fifth cause of death from cancer overall (458,000 deaths in 2008), but it is still the most frequent cause of cancer death in women in both developing (269,000 deaths, 12.7% of total) and developed regions (189,000) (1). In the United States, during 2011, the estimated new breast cancer cases are 229,060 and the estimated deaths amount to 39,920, for both sexes (breast cancer can also occur in men, although rarely)(2).

Many countries have launched national screening programs for breast cancer awareness and follow-up of subjects with high or middle average risk to develop this disease (e.g., family history of breast cancer, women over 50 years of age, etc.). Mammography is still the only test used for all breast cancer national screening programs; no screening test has ever been more carefully studied than screening mammography. In the past 50 years, more than 600,000 women have participated in 10 randomized trials, each involving approximately 10 years of follow-up (3). The outcome of this assessment is mixed: in a study, the U.S. Preventive Services Task Force estimated the reduction in mortality of approximately 15%-23%. They attributed this improvement mainly to the improvements in screening by mammography (4); but opposite conclusions were derived from other studies, for example (5), where the authors state that despite 30 years of increasingly prevalent use of screening mammograms, the expected mortality benefits have failed to materialize in either trial results or public health data. Moreover, in a Norwegian study the high level of mortality reduction published by the U.S. Services Task Force is challenged (6). The study of Kalager et al. provides additional data pointing at a modest benefit of mammography: making use of the opportunity provided by the systematic screening programs in Norway, the investigators singled out other parameters, such as increased breast-cancer awareness and improvements in treatment. They conclude that the benefit of the Norwegian screening program was small: a 10% reduction in breast-cancer mortality among women between the ages of 50 and 69 years. In this study, with a 10-year course of screening mammography for 2500 women of age 50, the estimated benefit for one woman avoiding to die from breast cancer were contrasted to the estimated harms of up to 1000 women having at least one "false alarm", about half of whom undergoing biopsy and to 5 to 15 women being misdiagnosed as having breast cancer, and consequently being treated needlessly (7).

These studies emphasize the need for further research into new methods of screening and improved therapy for this important disease that is killing thousands of women worldwide every year. (8)

SUMMARY

Testing the methylation status of a combination of several genes provides a highly sensitive and highly specific non-invasive tumor diagnosis for early stage breast cancer. The low-cost tests can use easily obtained samples such as blood, serum, plasma, saliva, or urine.

In one aspect, a highly specific and highly selective method of detecting breast cancer in a patient, includes obtaining a DNA sample from the patient; and measuring, from the DNA sample, a methylation level in a regulatory region of each of a plurality of genes selected from the group consisting of: FOXC1, ARFGEF1, CREBBP, MSH6, ARHGEF7, GNG4, RPIA, SLC2A14, BTG3, EDNRB, PRDM16, SST, HS3ST2, ITGA9, CDH1, Hoxa7, BMP6, CD40, and TNFRSF8.

The method can further include comparing the measured methylation level for each of the plurality of genes to a respective threshold methylation level, and, based on the comparisons, detecting the presence or absence of breast cancer in the patient with high sensitivity and high specificity. The presence or absence of breast cancer can be detected with a sensitivity of greater than 95% and a specificity of greater than 95%, or with a sensitivity of greater than 99% and a specificity of greater than 99% based on the comparisons.

The plurality of genes can include nine or more of the genes listed. The DNA sample can be obtained from a body fluid, wherein the body fluid is blood, serum, plasma, saliva, urine, stool, tissue, or a combination thereof.

The genes can be the genes of BC Set 1: ARFGEF1, ARHGEF7, CD40, CDH1, CREBBP, HS3ST2, RPIA, SST, and TNFRSF8.

The genes can be the genes of BC Set 2: ARFGEF1, ARHGE7, CD40, CDH1, HS3ST2, RPIA, SLC2A14, SST, and TNFRSF8.

The genes can be the genes of BC Set 3: ARFGEF1, ARHGE7, CDH1, CREBBP, HS3ST2, RPIA, SLC2A14, SST, and TNFRSF8.

The genes can be the genes of BC Set 4: ARFGEF1, CD40, CDH1, CREBBP, HS3ST2, RPIA, SLC2A14, SST, and TNFRSF8.

The genes can be the genes of BC Set 5: ARFGEF1, CDH1, CREBBP, HS3ST2, PRDM16, RPIA, SLC2A14, SST, and TNFRSF8.

Other aspects, embodiments, and features will be apparent from the following description, the drawings, and the claims.

DETAILED DESCRIPTION

Screening tests for cancer, particularly breast cancer, based on currently known biomarkers have low sensitivity and low specificity, and few of such tests are evaluated on body fluids. New combinations of biomarkers tested on readily and easily obtained body fluid samples can screen for breast cancer with high sensitivity and high specificity.

Sensitivity refers to the ability of a screening test to correctly identify true positives. For example, sensitivity can be expressed as a percentage, the proportion of actual positives which are correctly identified as such (e.g., the percentage of test subjects having cancer correctly identified by the test as having cancer). A test with high sensitivity has a low rate of false negatives.

Specificity refers to the ability of a screening test to correctly identify true negatives. For example, specificity can be expressed as a percentage, the proportion of actual negatives which are correctly identified as such (e.g., the percentage of test subjects not having cancer correctly identified by the test as not having cancer). A test with high specificity has a low rate of false positives.

Using a test based on a combination of biomarkers provides a screening test for breast cancer that can have higher sensitivity, higher specificity, or both higher sensitivity and higher specificity, than tests based on a single biomarker. Preferably a screening test has high levels of both sensitivity and specificity.

Alterations of DNA methylation patterns have been recognized as a common change in human cancers. Aberrant methylation of normally unmethylated CpG islands in or near the promoter region of many genes has been associated with transcriptional inactivation of important genes, including tumor suppressor genes, DNA repair genes, and metastasis inhibitor genes. Therefore, detection of aberrant promoter methylation of cancer-related genes can be an efficient method for the diagnosis, prognosis and/or detection of tumors.

A challenge in identifying DNA methylation patterns is that 5-methylcytosine is indistinguishable from cytosine in its hybridization behavior. The specific reaction of bisulfite with cytosine is therefore useful in investigating DNA methylation. Bisulfite can convert cytosine, but not 5-methylcytosine, to uracil. Uracil corresponds in its base-pairing behavior to thymidine, and thus allows 5-methylcytosine to be differentiated from cytosine using "standard" molecular biological techniques, for example, by amplification and hybridization or sequencing. An older method incorporates the DNA to be investigated in an agarose matrix, through which diffusion and renaturation of the DNA is prevented (bisulfite reacts only on single-stranded DNA) and all precipitation and purification steps are replaced by rapid dialysis (11). Individual cells can be investigated with this method, which illustrates the potential of the method. Of course, previously, only individual regions of up to approximately 3000 base pairs in length have been investigated; a global investigation of cells for thousands of possible methylation analyses is not possible. Of course, this method also cannot reliably analyze very small fragments of small sample quantities. These are lost despite the protection from diffusion through the matrix. Other known methods for detecting 5-methylcytosines are described by Rein et al. (12) and Cottrell (13).

Techniques such as methylation-specific arbitrarily primed PCR, methylated CpG island amplification (MCA), differential methylation hybridization (DMH), and restriction landmark genomic scanning (RLGS) take advantage of methylation-specific restriction enzymes to scan the genome for aberrantly methylated CpG sites. The advantage of these methods is that they directly look for methylation differences. In contrast, candidates can also be identified indirectly using gene expression studies. Gene expression in cell lines treated with 5-azacytidine can be compared to mock-treated cell lines to find genes activated by this de-methylating agent. Some genes in the literature, such as known tumor suppressor genes with CpG islands, are also good candidates.

Further analysis of these marker candidates requires higher throughput methodology. By far the most commonly used assay in research labs is methylation specific-PCR (MSP) or the real-time version (MethyLight). The sample DNA is treated with sodium bisulphite to convert unmethylated cytosines to uracils, while methylated cytosines remain intact. In a gel based MSP assay, one set of primers amplifies the unmethylated version and one set amplifies the methylated version, and the presence of a band on a gel in each reaction determines the methylation state. In the real-time version, amplification with methylation specific primers with or without probes is normalized to the total amount of input DNA to determine the fraction of DNA methylated for each region of interest. Alternative marker analysis methods include oligonucleotide arrays, primer extension, and sequencing.

Biomarkers for cancer were identified in the following way. Public gene expression data for normal and cancer cells was mined to identify genes showing reduced expression levels in cancer cells compared to normal cells. Those genes having reduced expression levels in cancer and CpG promoter islands were further investigated. It is generally known that reduced expression levels for genes with CpG islands is correlated with methylation of the CpG islands. For each of the genes selected for further investigation, a quantitative correlation between expression level and extent of methylation was established. Then, based on that quantitative correlation, a threshold methylation level was established for each gene. The threshold level was set as the highest extent of methylation seen in the normal samples, plus an additional amount, e.g., 5%, 10%, 25%, 33%, etc.

The predictive value of these biomarkers was tested. Again, methylation levels of the genes was determined for a group of normal samples and cancer samples, based on publicly available expression data and the quantitative correlation. For each gene in each sample, the methylation level was compared to the threshold for that gene. If the methylation level was higher than the threshold, that gene was scored as "true" (i.e., predictive of the presence of cancer) for that sample, or, if the methylation level was below the threshold, that gene was scored as "false" (i.e., predictive of the absence of cancer) for that sample. The sensitivity and specificity of several suitably chosen combinations of genes, for correctly predicting the presence or absence of cancer, was then determined based on the scores as defined above.

Thus, in clinical use, the biomarkers can be used in the following way. A DNA sample is obtained from a subject. The DNA sample can derived from any suitable source, including but not limited to blood, serum, plasma, saliva, urine, stool, tissue, or a combination of these. Preferably the DNA sample is derived from a source other than tissue; e.g., blood, serum, plasma, saliva, or urine. The methylation status of several the biomarker genes identified in the manner described above is then tested by any suitable method for determining the extent of DNA methylation, including but not limited to methylation specific PCR; methylated CpG island amplification; differential methylation hybridization; or restriction landmark genomic scanning. Advantageously, the assessment of methylation is a very stable procedure since, unlike, e.g., measuring mRNA levels, it is much less influenced by experimental parameters. This makes the test efficient for use by any clinical laboratory. The experimentally determined methylation levels for each gene are first compared to their respective threshold levels, and scored as true or false. Advantageously, by using a combination of biomarkers instead of a single marker, the result of the test is both highly sensitive and highly specific. The test can have a sensitivity of no less than 90%, no less than 95%, no less than 96%, no less than 97%, no less than 98%, no less than 99%, or 100%. The test can have a specificity of no less than 90%, no less than 95%, no less than 96%, no less than 97%, no less than 98%, no less than 99%, or 100%. In some instances, both sensitivity and specificity can be no less than 90%, no less than 95%, no less than 96%, no less than 97%, no less than 98%, no less than 99%, or 100%.

All the biomarkers already published and/or patented have low sensitivity and low specificity and few of them are evaluated on body fluid. The present combinations of the biomarkers proposed in this invention are unique for the diagnosis of BC patients.

Using a new computational methodology and available public data, a set of biomarkers—methylated promoter regions of a set of genes—for breast cancer were identified and then validated in different combinations. The genes were known and some have been previously identified as biomarkers for cancers, but the set, and the combinations of genes from within the set, are new.

Based on our study we identified genes whose combined methylation patterns provide 97% of sensitivity and 100% of specificity for BC diagnosis based on our data set of 32 BC patients and 32 BC-free individuals who have surgery for mammoplasty reduction. Even subsets of these genes secure 97% of sensitivity and 100% of specificity for BC diagnosis. These methylation pattern combinations have never been described before for the screening, or diagnosis or prognosis of BC. Moreover, the assessment of methylation is a very stable procedure since, unlike, e.g., measuring mRNA levels, it is much less influenced by experimental parameters. This makes the test efficient for use by any clinical laboratory.

The base set of genes identified is as follows:

Base BC Set: FOXC1, ARFGEF1, CREBBP, MSH6, ARHGEF7, GNG4, RPIA, SLC2A14, BTG3, EDNRB, PRDM16, SST, HS3ST2, ITGA9, CDH1, Hoxa7, BMP6, CD40, and TNFRSF8.

A test based methylation status of all nineteen of these genes provides 97% sensitivity and 100% specificity for breast cancer based on our data (see above). Tests based on smaller sets (e.g., sets of nine or more) of these genes can also provide 97% sensitivity and 100% specificity for breast cancer. Those smaller sets include:

BC Set 1: ARFGEF1, ARHGEF7, CD40, CDH1, CREBBP, HS3ST2, RPIA, SST, and TNFRSF8.

BC Set 2: ARFGEF1, ARHGE7, CD40, CDH1, HS3ST2, RPIA, SLC2A14, SST, and TNFRSF8.

BC Set 3: ARFGEF1, ARHGE7, CDH1, CREBBP, HS3ST2, RPIA, SLC2A14, SST, and TNFRSF8.

BC Set 4: ARFGEF1, CD40, CDH1, CREBBP, HS3ST2, RPIA, SLC2A14, SST, and TNFRSF8.

BC Set 5: ARFGEF1, CDH1, CREBBP, HS3ST2, PRDM16, RPIA, SLC2A14, SST, and TNFRSF8.

EXAMPLES

From 1787 publications, we selected 345 genes identified hyper-methylated in tumor of breast cancer patients when compared to normal tissues. The expression level of 221 from these 345 genes were found in two independent studies, the first study, assessed the expression of these genes in 18 autologous histologically normal breast epithelium from ER–or ER+ breast cancer patient compared to 18 reduction mammoplasty from normal subjects (9) and the second study the same genes (221) were assessed in 14 autologous normal tissue from breast cancer patient compared to 15 normal tissue taken for reduction mammoplasty also (10). Pooled together the data from the two studies and using a computational method, we inferred the methylation in serum based on gene expression for all these 221 in the 32 breast cancer patients and the 33 normal subjects cancer-free. From these 221 genes, 19 genes show a as potential screening markers for breast cancer at high level of sensitivity and specificity even over 5% of threshold (highest methylation value in normal patients+an error margin of 0.05. The error margin is defined as 0.05 times the difference between the full methylation value (100% methylation) and the highest methylation value in controls).

From this set of 221 genes, the 19 genes described in what follows are predicted hypermethylated in BC versus normal, rank among the best p-values using Wilcoxon signed-rank test or among the most discriminating ones based on the threshold, and keep their ability to discriminate under stringent conditions: FOXC1 (Gene ID: 2296), ARFGEF1 (Gene ID: 10565), CREBBP (Gene ID: 1387), MSH6 (Gene ID: 2956), ARHGEF7 (Gene ID: 8874), GNG4 (Gene ID: 2786), RPIA (Gene ID: 22934), SLC2A14 (Gene ID: 144195), BTG3 (Gene ID: 10950), EDNRB (Gene ID: 1910), PRDM16 (Gene ID: 63976), SST (Gene ID: 6750), HS3ST2 (Gene ID: 9956), ITGA9 (Gene ID: 3680), CDH1 (Gene ID: 999), Hoxa7 (Gene ID: 3204), BMP6 (Gene ID: 654), CD40 (Gene ID: 958) and TNFRSF8 (Gene ID: 943).

Table 1 shows predicted methylation values from the 32 breast cancer patients. Values shown: the calls for the 32 BC patients, defined as: "TRUE": the serum predicted methylation value is above the 5% threshold; "FALSE": the serum predicted methylation value is below the threshold. The combination of 19 biomarkers described in the table affords 97% sensitivity and 100% of specificity when asking a least one "TRUE" call to be diagnosed as having BC.

TABLE 1

| | Sample | FOXC1 | ARFGEF1 | CREBBP | MSH6 | ARHGEF7 | GNG4 | RPIA | SLC2A1 | BTG3 | EDNRB |
|---|---|---|---|---|---|---|---|---|---|---|---|
| Auto- | 212014 | F | F | F | F | F | F | F | F | F | F |
| logous | 212015 | T | F | F | F | F | T | F | F | F | F |
| normal | 212016 | F | T | T | T | F | F | F | T | T | F |
| tissue | 212017 | F | F | F | F | F | F | F | F | F | F |
| breast | 212018 | F | T | F | F | F | F | F | F | F | F |
| cancer | 212019 | F | T | F | T | F | F | F | F | F | F |
| patients | 212020 | F | F | T | T | T | T | T | F | F | F |
| | 212021 | T | F | T | F | T | T | T | T | F | F |
| | 212022 | T | T | F | F | F | T | F | F | T | F |
| | 212023 | F | T | F | F | F | T | F | F | T | F |

TABLE 1-continued

| | Sample | | | | | | | | | |
|---|---|---|---|---|---|---|---|---|---|---|
| | 212024 | T | F | F | F | F | T | F | F | F | F |
| | 212025 | F | F | F | T | F | T | F | F | T | F |
| | 212026 | T | F | F | F | F | F | F | T | T | T |
| | 212027 | T | F | F | F | F | T | F | T | F | T |
| Autologue to ER+ breast cancer | 512557 | F | T | F | F | F | F | F | F | F | F |
| | 512558 | T | F | F | F | F | F | F | F | F | F |
| | 512559 | F | F | F | F | F | F | F | F | F | F |
| | 512560 | F | F | F | F | F | F | F | F | F | F |
| | 512561 | F | T | T | T | T | F | F | T | T | F |
| | 512562 | F | F | T | T | F | F | F | F | F | F |
| | 212563 | F | F | F | F | F | F | F | F | F | F |
| | 512564 | T | F | T | F | T | T | F | T | F | T |
| | 512565 | T | F | T | T | F | F | T | F | F | T |
| Autologue to ER– breast cancer | 512566 | T | T | F | F | T | F | F | F | F | F |
| | 512567 | F | F | F | F | T | F | T | F | F | T |
| | 512568 | T | T | F | T | T | F | T | T | F | F |
| | 512569 | T | F | T | F | T | F | T | T | F | T |
| | 512570 | F | F | T | F | F | F | T | F | F | F |
| | 512571 | T | F | T | T | F | F | F | F | T | T |
| | 512572 | F | T | F | F | T | F | T | F | F | F |
| | 512573 | F | T | F | F | F | F | F | T | T | F |
| | 512574 | F | F | T | F | F | F | T | F | F | T |

| | Sample | PRDM16 | SST | HS3ST2 | ITGA9 | CDH1 | BMP6 | HOXA7 | CD40 | TNFRSF8 |
|---|---|---|---|---|---|---|---|---|---|---|
| Autologous normal tissue breast cancer patients | 212014 | F | F | F | F | F | F | F | F | F |
| | 212015 | F | F | T | F | F | T | F | F | T |
| | 212016 | F | F | T | T | T | F | F | F | F |
| | 212017 | F | T | F | T | F | F | F | F | F |
| | 212018 | T | F | F | F | F | F | F | F | F |
| | 212019 | F | F | F | F | T | F | F | F | F |
| | 212020 | F | F | F | F | F | F | F | F | F |
| | 212021 | F | F | F | F | F | T | F | F | F |
| | 212022 | F | F | T | F | F | F | F | F | F |
| | 212023 | F | F | F | F | T | F | F | F | F |
| | 212024 | T | T | T | F | F | F | T | T | T |
| | 212025 | T | T | F | F | F | F | T | F | T |
| | 212026 | F | T | F | F | F | F | F | T | F |
| | 212027 | T | T | T | T | F | F | F | T | T |
| Autologue to ER+ breast cancer | 512557 | F | F | F | F | T | F | F | F | F |
| | 512558 | F | F | F | F | F | F | T | F | F |
| | 512559 | F | F | F | F | F | F | T | F | F |
| | 512560 | F | F | F | F | F | F | T | F | F |
| | 512561 | F | F | F | F | T | F | F | F | F |
| | 512562 | F | T | T | F | F | F | F | F | T |
| | 212563 | T | T | F | F | F | F | T | F | T |
| | 512564 | T | F | F | T | F | T | F | T | F |
| | 512565 | F | F | F | F | F | F | F | F | F |
| Autologue to ER– breast cancer | 512566 | F | F | F | F | F | F | F | F | F |
| | 512567 | F | F | F | F | F | T | F | F | F |
| | 512568 | F | F | T | F | F | F | F | F | F |
| | 512569 | F | F | F | F | F | T | T | T | F |
| | 512570 | F | F | F | F | F | F | F | F | F |
| | 512571 | T | F | F | F | F | T | T | F | F |
| | 512572 | F | F | F | T | F | F | F | F | F |
| | 512573 | F | F | F | F | T | F | F | F | F |
| | 512574 | F | F | F | F | F | F | F | F | F |

REFERENCES

Each of the following references is incorporated by reference in its entirety.

(1) Breast Cancer Incidence, Mortality and Prevalence Worldwide in 2008, Summary Globocane 2008

(2) Siegel R, Naishadham D, Jemal A. Cancer statistics, 2012. CA Cancer J Clin. 2012 January; 62 (1):10-29

(3) H. Gilbert Welch, M.D., M.P.H. NEJM, Sep. 23, 2010; 363:1276-127

(4) Mandelblatt J S, Cronin K A, Bailey S, et al. Effects of mammography screening under different screening schedules: model estimates of potential benefits and harms. Ann Intern Med, 2009; 151:738-47

(5) Esserman L, Shieh Y, Thompson I. Rethinking screening for breast cancer and prostate cancer, JAMA 2009; 302:1685-1692

(6) Kalager M, Zelen M, Langmark F, Adami H. O. Effect of screening mammography on breast-cancer mortality in Norway. NEJM 2010; 363:1203-10

(7) H. Gilbert Welch, M.D., M.P.H. NEJM Sep. 23, 2010; 363:1276-1278

(8) David H. Newman, NEJM. 2012 January 12;366 (2):191; author reply 191-2

(9) Graham et al British Journal of Cancer (2010) 102, 1284-1293

(10) Anusri Triphati et al. Int. J. Cancer: 122, 1557-1566 (2008)

(11) Olek A., Oswald J., Walter J. A modified and improved method for bisulphate based cytosine methylation analysis. Nucleic Acids Res. 1996 December 15; 24 (24): 5064-6

(12) Rein T, DePamphilis M L, Zorbas H. Identifying 5-methylcytosine and related modifications in DNA genomes. Nucleic Acids Res. 1998 May 15; 26 (10): 2255-64

(13) Cottrell, S., Molecular diagnostic applications of DNA methylation technology, CLI October 2005.

Other embodiments are within the scope of the following claims.

What is claimed is:

1. A method comprising:
   measuring, in a DNA sample obtained from a patient, methylation level in a CpG promoter island of each gene in a set of genes, wherein the set of genes consists of FOXC1, ARFGEF1, CREBBP, MSH6, ARHGEF7, GNG4, RPIA, SLC2A14, BTG3, EDNRB, PRDM16, HS3ST2, ITGA9, CDH1, Hoxa7, BMP6, CD40, and TNFRSF8.

2. The method of claim 1, wherein the DNA sample is from blood, serum, plasma, saliva, urine, stool, tissue, or a combination thereof.

* * * * *